United States Patent
Dal-Molin

(10) Patent No.: US 6,591,131 B2
(45) Date of Patent: Jul. 8, 2003

(54) PROCESS FOR SAMPLING A CARDIAC PARAMETER, IN PARTICULAR AN INTRACARDIAC IMPEDANCE, IN AN ACTIVE IMPLANTABLE MEDICAL DEVICE SUCH AS PACEMAKER, DEFIBRILLATOR, CARDIOVERTOR AND/OR MULTISITE DEVICE

(75) Inventor: Renzo Dal-Molin, Chatillon (FR)

(73) Assignee: ELA Medical S.A., Montrouge (FR)

( * ) Notice: Subject to any disclaimer, the term of this patent is extended or adjusted under 35 U.S.C. 154(b) by 136 days.

(21) Appl. No.: 09/825,142

(22) Filed: Apr. 3, 2001

(65) Prior Publication Data

US 2002/0022783 A1 Feb. 21, 2002

(30) Foreign Application Priority Data

Apr. 7, 2000 (FR) .......................................... 00 04510

(51) Int. Cl.[7] .......................................... A61B 5/0245
(52) U.S. Cl. ...................................................... 600/510
(58) Field of Search .................................. 600/374, 510, 600/547, 508, 509; 607/4, 5, 9, 28, 7, 8, 16, 27

(56) References Cited

U.S. PATENT DOCUMENTS

| 5,503,160 A | * | 4/1996 | Pering et al. .................. 128/706 |
| 5,690,118 A | * | 11/1997 | Sornmo et al. ................. 128/696 |
| 5,836,889 A | * | 11/1998 | Wyborny et al. ............... 600/509 |
| 5,847,569 A | | 12/1998 | Ho et al. ........................ 324/752 |
| 6,445,947 B1 | * | 9/2002 | Hoium et al. ................... 600/515 |

* cited by examiner

Primary Examiner—George R. Evanisko
Assistant Examiner—Frances P. Oropeza
(74) Attorney, Agent, or Firm—Orrick, Herrington & Sutcliffe LLP

(57) ABSTRACT

A process for sampling a cardiac parameter, in particular an intracardiac impedance, in an active implantable medical device such as a pacemaker, defibrillator, cardioverter and/or multisite device. The process includes carrying out in a repeated manner over a plurality of successive cardiac cycles (CYCLE 1 ... CYCLE 8), the steps of detecting a moment (E) at which a ventricular event occurred, and then sampling the aforesaid signal during each cardiac cycle with a constant sampling step and a predetermined temporal shift ($\Delta t_1 \ldots \Delta t_8$) between the detected ventricular event and the first sample in each cycle, this temporal shift being a progressive variable shift from one cycle to the following cycle.

5 Claims, 1 Drawing Sheet

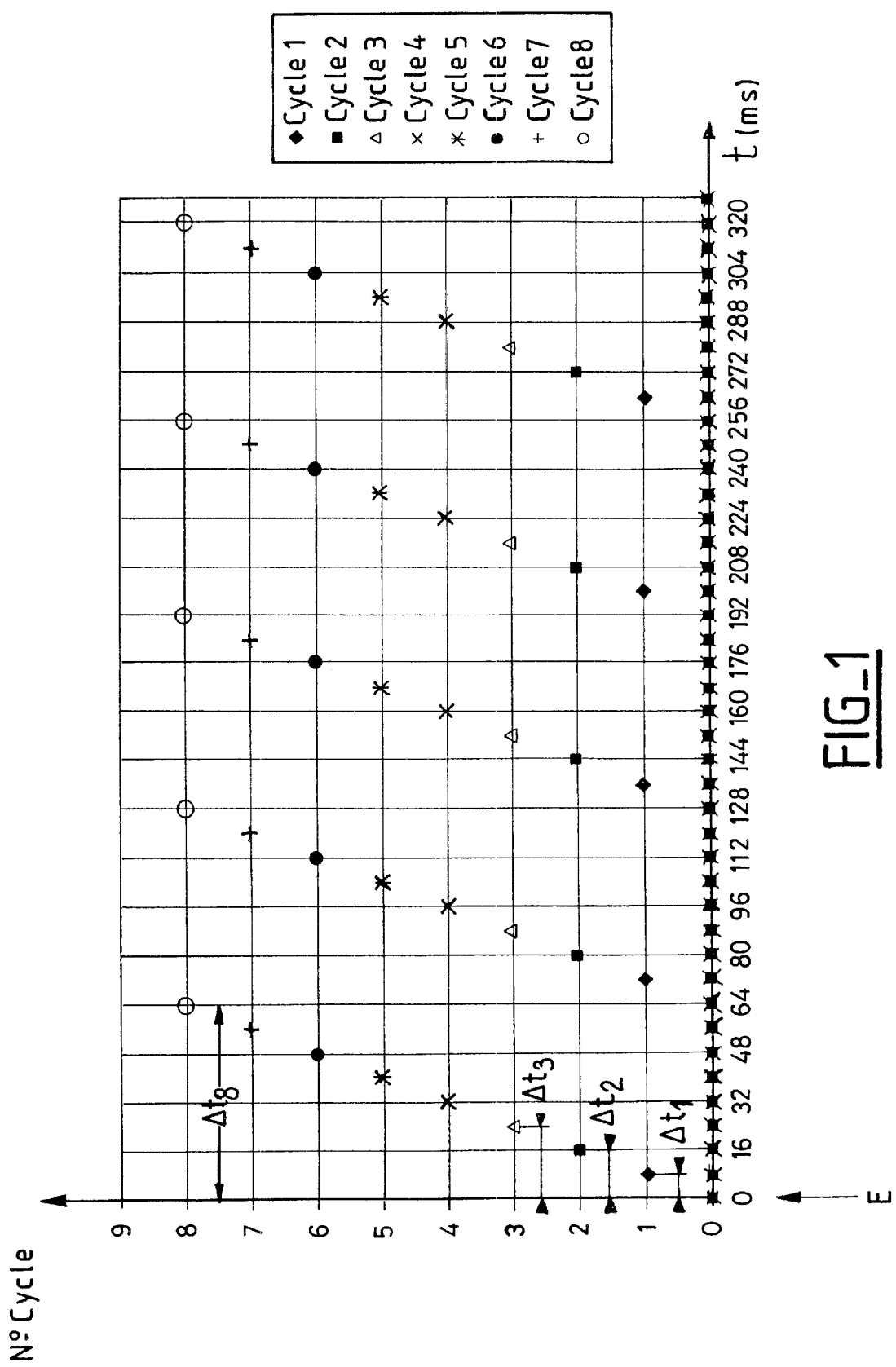
FIG_1

PROCESS FOR SAMPLING A CARDIAC PARAMETER, IN PARTICULAR AN INTRACARDIAC IMPEDANCE, IN AN ACTIVE IMPLANTABLE MEDICAL DEVICE SUCH AS PACEMAKER, DEFIBRILLATOR, CARDIOVERTOR AND/OR MULTISITE DEVICE

FIELD OF THE INVENTION

The present invention relates to "active implantable medical devices" as such devices are defined by the Jun. 20, 1990 directive 90/385/CEE of the Council of the European Communities, more particularly to pacemaker, defibrillator and/or cardiovertor devices that are able to deliver to the heart stimulation pulses of low energy for the treatment of heartbeat rate disorders.

BACKGROUND OF THE INVENTION

It is known to sense cardiac activity by detecting electronic signals in the body. From among these signals, cardiac parameters, such as impedance values, electrocardiograms, and the like, can be determined and used in monitoring and treating cardiac conditions. It is known, for example, to measure an intracardiac impedance, for examples, the interventricular impedance (between the right ventricle and the left ventricle) in a multisite type device, which is a useful parameter for controlling the re-synchronization of the ventricles, and the transvalvular impedance (between an atrium and ventricle on the same side of the heart) or the oblique trans-septum impedance (between right atrium and the left ventricle). These latter impedance values are correlated with the cardiac flow and make it possible, in particular, to obtain an indication of the "fraction of ejection," which is a hemodynamic reference parameter for the optimization of stimulation on the various sites of a multisite device.

In the prior known systems, the cardiac parameter to be determined is sampled from a signal collected (sensed) by the implant device, typically with a sampling step of 16 ms, with the sampling and consequent measurement being repeated with each cardiac cycle. The data sampled is then used to determine the cardiac parameter in a known manner.

OBJECTS AND SUMMARY OF THE INVENTION

It is an object of the present invention to provide an improved sampling process, making it possible to determine a selected cardiac parameter while decreasing the number of collected samples required to determine the parameter, and consequently reducing the energy consumption of the implant. It is a further object to do so without deteriorating the quality of the determined result (which is related to the sampling rate, and which must be sufficiently high).

To this end, the present invention proposes to determine the selected cardiac parameter by carrying out, in a repeated manner, over a plurality of successive cardiac cycles, the detection of the moment of occurrence of a distinct cardiac event, and sampling the signal from which the aforesaid cardiac parameter will be determined during the cardiac cycles with a constant sampling step and a predetermined temporal shift between the occurrence of the detected cardiac event and the first sample of each cycle, such that the temporal shift is a variable progressive shift from one cycle to the following cycle. Preferably, the maximum duration of the variable temporal shift is always less than the duration of the current cycle, and increases by a constant increment from one cycle to the following cycle. Once the samples are obtained for a given number of successive cardiac cycles, the collected samples can be synchronized with reference to the distinct cardiac event of each cycle, and averaged or smoothed to provide a representative signal which is used to determine the aforesaid cardiac parameter. Preferably, the distinct cardiac event is one which can be used to indicate a cardiac cycle frequency, for example, a ventricular event (a spontaneous detection or a stimulation). It is possible, however, to use other events.

BRIEF DESCRIPTION OF THE DRAWING

Further features, advantages and characteristics of the present invention will become apparent to a person of ordinary skill in the art in view of the following detailed description of the invention, made with reference to the annexed drawing, which is a diagram showing the relative distribution of the sampling during a plurality of successive cardiac cycles.

DETAILED DESCRIPTION OF THE INVENTION

One of the considerations underlying the present invention is the fact that the cardiac parameters which one wishes to measure, like the intracardiac impedance, evolve over time as the blood flows. In addition, the evolution is relatively slow in comparison to the scale of the duration of a cardiac cycle, if the state of the patient is relatively stable and in the absence of frequent disorders of the heart rate.

It has been discovered by the inventor that it is possible to distribute the measurement of the cardiac parameter over several successive cardiac cycles, without notably deteriorating the quality of the measurement obtained, when the multiple measurements are combined and the composition of the variations of the sampled values are considered.

By reducing the number of samples taken during each cycle, one will reduce, in the same proportion, the energy consumed by the circuits of the implant which operate the collection and the processing (signal conditioning, analog/digital conversion, storing, data smoothing (averaging), etc.) of the signal corresponding to the selected cardiac parameter. Thus, instead of making one measurement of the desired cardiac parameter over one cardiac cycle, for each cycle, it is, for example, possible to spread out the one measurement over a number of cycles, e.g., eight cycles by taking eight times fewer samples during each cycle. Advantageously, this reduces the energy consumption to make the measurement by about a factor of eight.

However, to be able to combine the measurements collected during the different cycles, it is necessary to have a precise reference point on which the different samplings will be synchronized. For this purpose, a temporal reference is selected, preferably the moment of the occurrence of a ventricular event. In other words, one takes as the origin of time the moment of detection of a depolarization, or the moment of a stimulation, of a ventricle, more preferably the right ventricle.

During the first cardiac cycle, a sampling is operated with a constant sampling step, for example 64 ms, and the first sample is taken with a given temporal shift $\Delta t_1$ compared to the moment of occurrence of the event, for example, an 8 ms shift. Sampling then continues for a given length of time, for example, a duration of 320 ms following the ventricular event. In other words, for the first cycle, sampling is operated at 8, 72, 136, 200 and 264 ms after the ventricular event. These five points of sampling are illustrated on FIG. 1 by diamonds, the origin of time being the ventricular event E.

It will be noted that the chosen sampling step, here 64 ms, is much longer than the sampling step of the devices of prior art, which typically are 8 or 16 ms. This difference provides a correlative reduction of the consumption of the implant device in accordance with the present invention.

With the second cycle, one carries out a sampling with the same 64 ms step interval as previously, but with a temporal shift $\Delta t_2 = 16$ ms compared to the ventricular event E, instead of $\Delta t_1 = 8$ ms. The samples of this second cycle are thus collected at 16, 80, 144, 208 and 272 ms after the event E, as illustrated by the squares on FIG. 1. Thus, the samples of the second cycle are respectively shifted temporily relative to the samples of the first cycle.

One then proceeds in the same manner in the following cycles, by keeping the same sampling step in each subsequent cycle, but by gradually increasing the temporal shift $\Delta t_3, \Delta t_4 \ldots \Delta t_8$, using 8 ms as a constant increment (i.e. $\Delta t_1 = 8$ ms, $\Delta t_2 = 16$ ms $\ldots \Delta t_8 = 64$ ms).

At the end of the eighth cardiac cycle, if one chooses in a suitable manner the increment $\Delta t_i - \Delta t_{i-1}$ of the temporal shift $\Delta t_i$, one will have scanned the major part of the zone of the cardiac cycle to study with a "stroboscopic effect," by taking only a reduced number of samples during each cycle. At the end of the eight cycles in the described embodiment, one thus has forty samples. By superimposing the data, referenced to the event E, it is possible to form a composite data and determine the value, and the evolution, of the selected cardiac parameter.

The cardiac parameter could thus be evaluated at the end of eight cycles, then again at the end of sixteen cycles, etc. It also could be also evaluated more frequently, for example, on each subsequent cycle by combining the data acquired over the last eight cardiac cycles using a sliding "window" of data analysis, and using a smoothing (averaging) of the data, or any other similar technique.

The increment $\Delta t_i - \Delta t_{i-1}$ between two successive temporal shifts (which in the described example is 8 ms) is selected to be sufficiently low to make it possible to see the details of the variation of the signal during a cardiac cycle (Shannon Theory applied to the signal sampling). It also is selected to avoid an overlapping of the measurements taken during successive cycles, for example, to prevent a situation that the first sample collected in the eighth cycle (i.e., E+64 ms) is not acquired after the second sample collected during the first cycle (i.e., E+72 ms). The increment $\Delta t_i - \Delta t_{i-1}$ will, however, be selected sufficiently large to cover the entire zone in the cardiac cycle to be sampled.

In the illustrated example, there exists only a small interval between the first sample of the eighth cycle (at E+64 ms) and the second sample of the first cycle (at E+72 ms). This makes it possible to cover, in a complete and homogeneous manner, the zone [E; E+320 ms], i.e., the first 320 milliseconds of a cardiac cycle. In this regard, it is noted that the total duration of a cardiac cycle is typically about 860 ms at 70 bpm.

It should be understood that the increment $\Delta t_i - \Delta t_{i-1}$ need not be necessarily fixed. It can be dynamically varied according to the design needs or certain conditions, for example, it can be decreased in the event of a detected increase in the heart rate, and conversely.

The increment $\Delta t_i - \Delta t_{i-1}$ as well as the initial shift $\Delta t_i$ also can be selected so as to concentrate the analysis of the selected cardiac parameter during a "window" of a particular measure within the cardiac cycle, which does not raise a particular difficulty since during successive cycles the sampling remains synchronized on the ventricular event E.

It should be understood that, although the present invention has been described in the context of cardiac impedance measurements, it is not so restrictive, and indeed the invention also applies to the measurement of other intracardiac parameters, for example, the analysis of an intracardiac electrocardiogram, or similar applications. One skilled in the art also will appreciate that the present invention can be practiced by other than the described embodiments, and by use of numerical values for the variables other than those described herein, which are presented for the purposes of illustration and not of limitation.

I claim:

1. A process for determining a cardiac parameter from a signal collected by an active implantable medical device, comprising carrying out in a repeated manner over a plurality of successive cardiac cycles, the steps of:

detecting a moment (E) a distinct cardiac event has occurred; and sampling a signal corresponding to said cardiac parameter during each of said plurality of successive cycles, with a constant sampling step and a predetermined temporal shift between the detected distinct cardiac event and the first sample in each cycle, said temporal shift being a variable progressive shift from one cycle to the following cycle in said plurality of successive cycles.

2. The process of claim 1, wherein each current cycle of said plurality of successive cycles has a duration, further comprising providing the variable temporal shift ($\Delta t_i$) with a maximum duration that is less than the duration of a current cycle of said plurality of successive cycles.

3. The process of claim 1, further comprising increasing the duration of the variable temporal shift ($\Delta t_1$) by a constant increment ($\Delta t_1 - \Delta t_{i-1}$) from one cycle to the following cycle.

4. The process of claim 1, further comprising collecting said samples over a number of successive cycles synchronized to said moment of said distinct cardiac event, and smoothing said collected samples to provide a representative signal corresponding to said cardiac parameter.

5. The process of claim 4, wherein detecting the moment of said distinct cardiac event further comprises detecting the moment of a ventricular event.

* * * * *